United States Patent
Kollgaard et al.

(10) Patent No.: US 7,320,241 B2
(45) Date of Patent: Jan. 22, 2008

(54) ULTRASONIC INSPECTION REFERENCE STANDARD FOR COMPOSITE MATERIALS

(75) Inventors: Jeffrey R. Kollgaard, Kent, WA (US); David Truong, Seattle, WA (US)

(73) Assignee: The Boeing Company, Chicago, IL (US)

( * ) Notice: Subject to any disclaimer, the term of this patent is extended or adjusted under 35 U.S.C. 154(b) by 124 days.

(21) Appl. No.: 11/267,671

(22) Filed: Nov. 4, 2005

(65) Prior Publication Data

US 2007/0101815 A1     May 10, 2007

(51) Int. Cl.
*G01N 29/30*     (2006.01)
(52) U.S. Cl. ...................................... 73/1.86
(58) Field of Classification Search ........... 73/1.86, 73/865.6, 1.82
See application file for complete search history.

(56) References Cited

U.S. PATENT DOCUMENTS

| | | | |
|---|---|---|---|
| 5,054,310 A * | 10/1991 | Flynn .......................... 73/1.86 |
| 5,312,755 A * | 5/1994 | Madsen et al. ................. 436/8 |
| 5,656,763 A * | 8/1997 | Flax ............................ 73/1.82 |
| 6,238,343 B1 * | 5/2001 | Madsen et al. .............. 73/1.86 |
| 6,405,583 B1 * | 6/2002 | Shirakawabe et al. ....... 73/1.86 |
| 2006/0213250 A1 * | 9/2006 | Vaccaro et al. ............. 73/1.86 |

FOREIGN PATENT DOCUMENTS

WO     WO 9013024 A1 * 11/1990

* cited by examiner

*Primary Examiner*—Daniel S. Larkin
*Assistant Examiner*—Nashmiya Fayyaz
(74) *Attorney, Agent, or Firm*—Ingrassia Fisher & Lorenz, P.C.

(57) ABSTRACT

An ultrasonic inspection reference standard for a composite material includes a block comprising the composite material. The block further comprises a first plurality of parallel rectangular-shaped channels within the block and a second plurality of parallel rectangular-shaped channels within the block, wherein the second plurality of channels extend at about a ninety degree angle to the first plurality of channels and wherein the second plurality of channels is located on a separate plane as the first plurality of channels.

12 Claims, 4 Drawing Sheets

ULTRASONIC INSPECTION REFERENCE STANDARD FOR COMPOSITE MATERIALS

BACKGROUND OF THE INVENTION

The present invention generally relates to non-destructive testing of materials and, more particularly, to the generation of reference standards for acoustic non-destructive testing of porous materials.

Composite laminate structures have been finding increasing application in commercial passenger aircraft, such as the Boeing 787 passenger jet in which large areas of the wing, empennage, and fuselage are constructed of carbon laminates. Portions of an aircraft that are considered to be a part of the primary structure have stringent inspection requirements associated with them. Therefore, those portions of the primary structure constructed of porous materials such as carbon laminate must pass rigorous testing. As a result, methods for inspecting these porous materials must reliably detect and quantify delaminations, foreign material inclusions, and porosity in the materials.

In the case of porosity, quantitative evaluation is a complex problem. Porosity is an allowable condition up to a certain extent. Measuring porosity nondestructively requires the use of ultrasonics, wherein the acoustic response of the part being tested is compared to porosity calibration standards (i.e., reference standards) of similar thickness containing known levels of porosity. FIG. 1 is an image 100 of an acoustic impression of a test material, such as a composite material. FIG. 1 illustrates ultrasonic data from a composite laminate with porosity. The image 100 is garnered using a non-destructive ultrasonic apparatus, such as a transducer, a through transmission transducer, a pulse echo transducer or an eddy current transducer. FIG. 1 shows two areas of the laminate having differing porosity readings. The first area 102 shows an area of high porosity. The second area 104 shows an area of low porosity.

Currently, porosity calibration standards are produced using an "exact analog" method wherein actual composite parts containing varying levels of porosity are produced. The ultrasonic attenuation of these porosity calibration standards is used to produce curves of attenuation versus porosity level. These attenuation curves are then compared to readings taken from the parts being tested. This approach, however, does not come without its problems.

One problem with this approach is that the attenuation curve represented by the porosity calibration standards can only be used with a particular inspection system because different instruments have different pulser and receiver characteristics, and transducers have different frequency bandwidths. In practice, this means that two ultrasonic testing systems using the same porosity calibration standards may produce different results. For example, a material having two percent porosity may register as 12 dB on a first ultrasonic testing system, but only 8 dB with a second ultrasonic testing system. Thus, if the porosity calibration curve for the first ultrasonic testing system is used by the operator of the second ultrasonic testing system, that operator would under-call the true porosity level in the part being tested. In order to ensure that different systems achieve the same results, the "exact analog" porosity calibration standards are produced in multiple sets—one set for each ultrasonic testing system—and shipped to each tester. This approach, therefore, requires the fabrication of multiple porosity calibration standards.

FIG. 2 is a chart 200 of an x-y plot showing a set of curves 212-217 indicating attenuation vs. thickness for a through-transmission technique using a conventional ultrasonic inspection reference standard. Attenuation is shown along the y-axis 202 measured in decibel (dB), while composite material thickness is shown on the x-axis 204 measured in inches. The attenuation is a decrease in intensity of a sound wave as a result of absorption of energy and of scattering out of the path of a receiving transducer.

Each of the six curves shown in the chart 200 represents the attenuation readings from a separate ultrasonic testing system, wherein all six ultrasonic testing systems used the same target composite part. Curve 212, for example, shows six separate data points representing readings garnered from an ultrasonic testing system. The curve 212 is extrapolated using the six readings. Each of the curves 213, 214, 215 and 216 also represent curves that were extrapolated using six separate data points representing readings garnered from a separate ultrasonic testing system. Curve 217 shows three separate data points representing readings garnered from another ultrasonic testing system. The curve 217 is extrapolated using the three readings.

As shown in the chart, each curve 212-217 represents the readings garnered from a different ultrasonic inspection system or inspection method but using the same test composite part. The reason for the difference in allowable attenuation is due to equipment variability from system to system or inspection method to inspection method. Examples of equipment variables that affect the attenuation curves include transducer type, transducer frequency, transducer diameter, transducer focal length, water column diameter in squirter systems, pulser type, system bandwidth, system dynamic range, and index dimension.

This approach requires the production of multiple porosity calibration standards. The standards are currently made by curing composite laminates with incremental cure variations intended to produce increased porosity. Once this is complete, the laminates are scanned with through-transmission ultrasonics. The process often produces laminates with spatially uneven levels of porosity, such that a relatively uniform area must be selected for independent verification of porosity level. The independent verification process involves comparison with master standards, if they exist, that have been inspected by the same system. If master standards do not exist, the part must be sectioned as close as possible to the area of interest and destructively examined for porosity level. The area of interest is then cut into coupons (or small rectangular patches) and engraved with the identified porosity level. This process must be repeated for each thickness that is necessary to produce data points in an attenuation curve, with at least eight thicknesses required, sometimes more.

While the technique described above has been used in production applications to make sets of porosity calibration standards, it is not considered satisfactory for the parallel problem of evaluating porosity in composite repairs when an aircraft is in service. Producing sets of porosity calibration standards for every airline and maintenance base is not practical due to time and money constraints. Faced with this problem, another acoustic substitute approach emerged. This method uses a phenolic step wedge as a porosity calibration standard that replicates the attenuation response from a threshold level (e.g., 4 percent) of porosity, which is the threshold rejectable level for porous materials. In the field, the inspector calibrates the ultrasonic testing system on the porosity calibration standard (i.e., the wedge) and then tests the part being repaired. If the reading from the part being repaired is lower than the reading from the standard, the part is rejected. Otherwise, the part is deemed acceptable for use.

The inspection using the approach above is a "go/no-go" decision. That is, the part being repaired is either acceptable (porosity below threshold level) or rejected (porosity above threshold level). In many cases the tester must know the actual porosity level of the part. With the go/no-go standard, the tester is not capable of providing this information.

Yet another acoustic substitute approach that emerged involved the use of circular channels embedded in blocks of composite materials. This method uses a composite block with the channels as a porosity calibration standard that attempted to replicate the attenuation response from an aircraft part with a given porosity value. This approach, however, was not successful, as the channels were not able to adequately replicate the attenuation response from an aircraft part with a given porosity value.

As can be seen, there is a need for an alternative approach to building porosity calibration standards for composite materials in order to reduce the cost of design, manufacturing, and qualification. Furthermore, there is a need for a method that enables the mass production of porosity calibration standards that can be used for ultrasonic inspection of composite materials due to the growing industrial application of composite materials and, therefore, an increased volume of composite parts to be inspected using ultrasonic inspection techniques.

SUMMARY OF THE INVENTION

In one aspect of the present invention, an ultrasonic inspection reference standard for a composite material includes a block comprising the composite material. The block further comprises a first plurality of parallel rectangular-shaped channels within the block and a second plurality of parallel rectangular-shaped channels within the block, wherein the second plurality of channels is located on a separate plane as the first plurality of channels.

In another aspect of the present invention, a system for inspecting composite materials comprises an ultrasonic inspection apparatus for ultrasonically scanning a material comprising a composite material. The system further includes a block comprising the composite material. The block comprises a first plurality of parallel channels within the block, wherein each channel includes a flat surface and each flat surface is co-planar. The block further comprises a second plurality of parallel channels within the block, wherein each channel includes a flat surface and each flat surface is co-planar, and wherein the second plurality of channels is located on a separate plane as the first plurality of channels.

In still another aspect of the present invention, an ultrasonic inspection process for composite materials comprises inspecting an ultrasonic inspection reference standard with an ultrasonic technique, the ultrasonic inspection reference standard comprising a block comprising a composite material, wherein the block includes a first plurality of parallel rectangular-shaped channels within the block and a second plurality of parallel rectangular-shaped channels within the block, wherein the second plurality of channels extend at about a ninety degree angle to the first plurality of channels and wherein the second plurality of channels is located on a separate plane as the first plurality of channels. The process further includes inspecting a composite part with the ultrasonic technique and comparing results of the inspecting of the ultrasonic inspection reference standard with results of the inspecting of the composite part.

These and other features, aspects and advantages of the present invention will become better understood with reference to the following drawings, description and claims.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides an ultrasonic inspection reference standard for composite materials that solves the problem of producing inexpensive, programmable porosity calibration standards (i.e., inspection reference standards) for testing composite materials. In one embodiment, the present invention provides an ultrasonic inspection reference standard that provides acoustic properties that are similar or identical to the acoustic properties of a composite material at significantly lower manufacturing cost. An embodiment of the present invention provides an ultrasonic inspection reference standard that is suitable for, but not limited to, ultrasonic inspection of composite parts used in the aircraft airframe industry, both commercial and defense.

In another embodiment, the present invention utilizes a stereo lithography process that can also be used, for example, for rapid prototyping, to manufacture an ultrasonic inspection reference standard that closely resembles the part under inspection. The stereo lithography process allows for the creation of parallel, rectangular-shaped channels in an ultrasonic inspection reference standard so as to adequately emulate known porosity levels in a composite material. Furthermore, by using the stereo lithography process to create an ultrasonic inspection reference standard for ultrasonic testing of composite materials, as in one embodiment of the present invention, the lay-up and machining time needed may be significantly reduced compared to the lay-up and machining time needed to produce a prior art reference standard. The stereo lithography process also enables the creation of an ultrasonic inspection reference standard according to one embodiment of the present invention with added versatility of geometry control compared to the manufacturing process for prior art composite reference standards.

Figure 1:
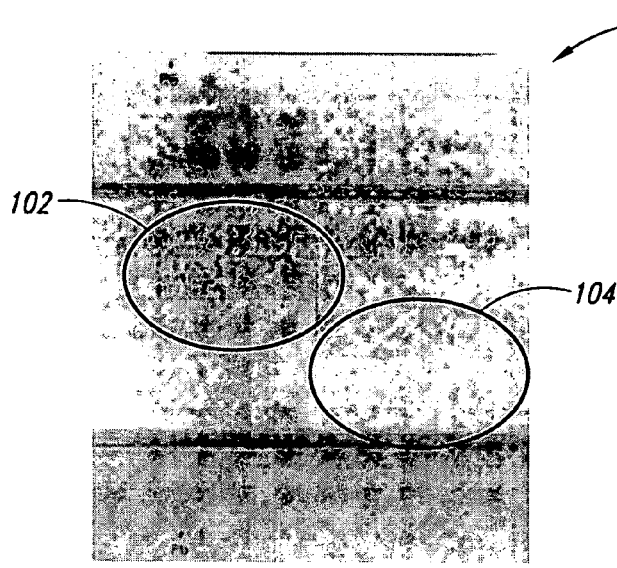
FIG. 1 is an image of an acoustic impression of a test material.
Figure 2:
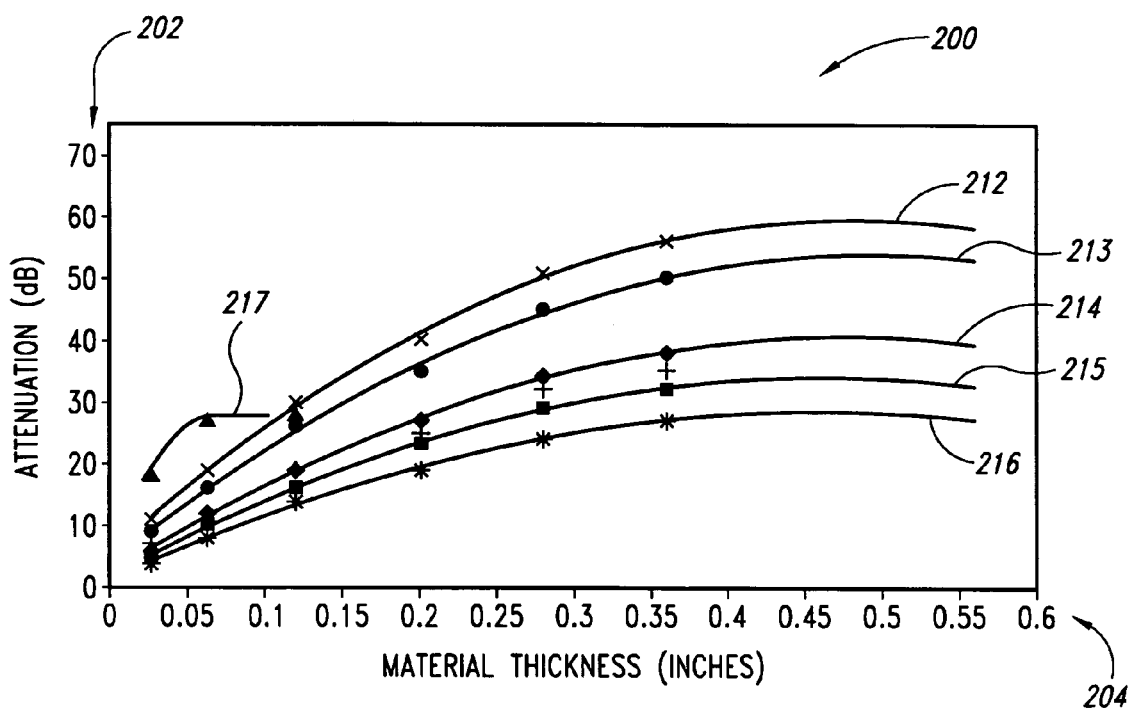
FIG. 2 is a chart of an x-y plot showing a set of curves indicating attenuation vs. thickness for a through-transmission technique using a conventional ultrasonic inspection reference standard.
Figure 3A:
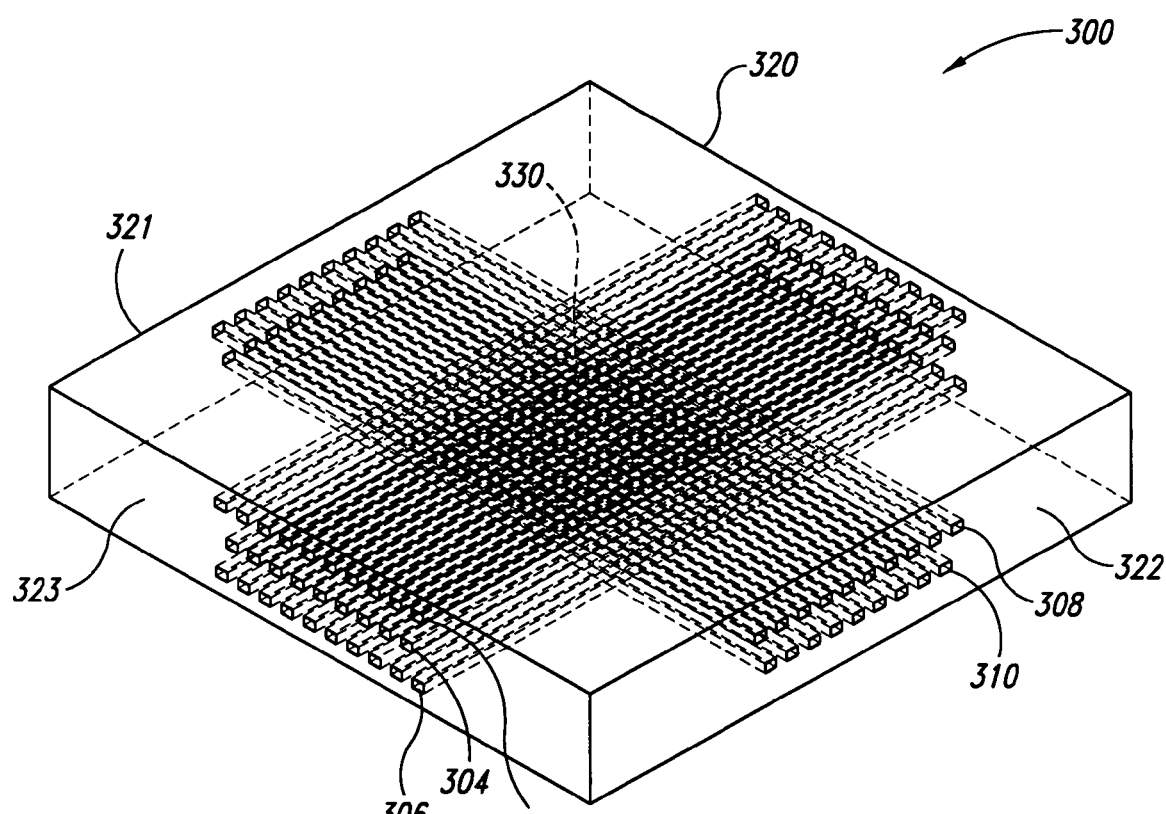
FIG. 3A is an illustration of a block used as an ultrasonic inspection reference standard according to one embodiment of the present invention.

FIG. 3A is an illustration of a block 300 used as an ultrasonic inspection reference standard according to one embodiment of the present invention. Block 300 can be constructed of any composite material including a laminate, graphite, any resin and fiber combination, and a non-fiber resin. Although in one embodiment of the present invention the block 300 is shown as a rectangular-shaped block, any shape of block 300 can be supported by the present invention.

FIG. 3A shows a first set 302 of ten rectangular-shaped channels that can be parallel to each other. The channels of the first set 302 are rectangular in that each channel is shaped as a three dimensional rectangular cube. The channels of the first set 302 are parallel in that the distance between any two channels remains the same along the length the channels. The channels of the first set 302 extend from one end 320 of the block 300 to the other end 323. Note that the channels of the first set 302 can be positioned at the same height, i.e., on the same plane.

In one embodiment of the present invention, the channels of the first set 302 and can be evenly spaced, whereby the distance (such as distance 363 of FIG. 3B) between all adjacent channels of the first set 302 is equal. In another embodiment of the present invention, the distance 363 between adjacent channels of the first set 302 can vary. In one embodiment of the present invention, the dimensions of each channel of the first set 302 can be congruent, i.e., the height 361, width 362 and length 360 of each channel (See FIG. 3B) can be identical. In another embodiment of the present invention, the dimensions of each channel of the first set 302 can vary.

FIG. 3A also shows a second set 304 of ten rectangular-shaped channels that can be parallel to each other. The channels of the second set 304 are rectangular and parallel in the same way as the channels of the first set 302. The channels of the second set 304 extend from one end 320 of the block 300 to the other end 323. Note that the channels of the second set 304 can be positioned at the same height, i.e., on the same plane, which is a height and plane lower than the channels of the first set 302. The channels of the second set 304 can be parallel to the channels of the first set 302.

Like the channels of the first set 302, the channels of the second set 304 can be evenly spaced or the distance between adjacent channels of the second set 304 can vary. Also like the channels of the first set 302, the dimensions of each channel of the second set 304 can be congruent or can vary.

FIG. 3A also shows a third set 306 of ten rectangular-shaped channels that can be parallel to each other. The channels of the third set 306 are rectangular and parallel in the same way as the channels of the first set 302. The channels of the third set 306 extend from one end 320 of the block 300 to the other end 323. Note that the channels of the third set 306 can be positioned at the same height, i.e., on the same plane, which is a height and plane lower than the channels of the first set 302 and the channels of the second set 304. The channels of the third set 306 can be parallel to the channels of the first set 302 and the channels of the second set 304.

Like the channels of the first set 302, the channels of the third set 306 can be evenly spaced or the distance between adjacent channels of the third set 306 can vary. Also like the channels of the first set 302, the dimensions of each channel of the third set 306 can be congruent or can vary.

FIG. 3A also shows a fourth set 308 of ten rectangular-shaped channels that can be parallel to each other. The channels of the fourth set 308 are rectangular and parallel in the same way as the channels of the first set 302. The channels of the fourth set 308 extend from one end 321 of the block 300 to the other end 322. Note that the channels of the fourth set 308 can be positioned at the same height, i.e., on the same plane, which is a height and plane lower than the channels of the first set 302 and higher than the channels of the second set 304. The channels of the fourth set 308 can be perpendicular to the channels of the first set 302, the second set 304 and the third set 306. That is, the direction of the channels of the fourth set 308 can be at a ninety degree angle to the direction of the channels of the first set 302, the second set 304 and the third set 306, although the channels of the fourth set 308 do not intersect with any other channels because each set of channels is positioned at a separate height or plane within the block 300.

Like the channels of the first set 302, the channels of the fourth set 308 can be evenly spaced or the distance between adjacent channels of the fourth set 308 can vary. Also like the channels of the first set 302, the dimensions of each channel of the fourth set 308 can be congruent or can vary.

FIG. 3A also shows a fifth set 310 of ten rectangular-shaped channels that can be parallel to each other. The channels of the fifth set 310 are rectangular and parallel in the same way as the channels of the first set 302. The channels of the fifth set 310 extend from one end 321 of the block 300 to the other end 322. Note that the channels of the fifth set 310 can be positioned at the same height, i.e., on the same plane, which is a height and plane lower than the channels of the second set 304 and higher than the channels of the third set 306. The channels of the fifth set 310 can be perpendicular to the channels of the first set 302, the second set 304 and the third set 306. That is, the direction of the channels of the fifth set 310 can be at a ninety degree angle to the direction of the channels of the first set 302, the second set 304 and the third set 306, although the channels of the fifth set 310 do not intersect with any other channels because each set of channels is positioned at a separate height or plane within the block 300. The channels of the fifth set 310 can be parallel to the channels of the fourth set 308.

Like the channels of the first set 302, the channels of the fifth set 310 can be evenly spaced or the distance between adjacent channels of the fifth set 310 can vary. Also like the channels of the first set 302, the dimensions of each channel of the fifth set 310 can be congruent or can vary.

FIG. 3A shows an area 330 wherein, from a perspective view, the direction of the channels of the first set 304, the second set 306 and the third set 308 intersect with the direction of the channels of the fourth set 308 and the fifth set 310. Again, there is no actual intersection of the channels, but rather from a top view the channels intersect in direction only. In an embodiment of the present invention, the area 330 can be a work area used as an ultrasonic inspection reference standard wherein a reading can be taken and later compared to a reading from a part being tested. Note that although FIG. 3A shows only ten rectangular channels in each set 302, 304, 306, 308 and 310, the present invention supports any number of channels in each set.

In one embodiment of the present invention, the block 300 used as an ultrasonic inspection reference standard has a porosity percentage value associated with it. This value indicates the porosity percentage value that can be emulated by the block 300. In another embodiment of the present invention, several blocks, such as block 300, can be used as an ultrasonic inspection reference standard, each block having a porosity percentage value associated with it. In one example, five to eight blocks can be used, wherein each block has a porosity percentage value associated with it; the porosity values ranging from 0% to 8%. In another example, nine blocks can be used, wherein each block is associated with one of the following porosity values: 0%, 1%, 2%, 3%, 4%, 5%, 6%, 7%, and 8%.

Figure 3B:
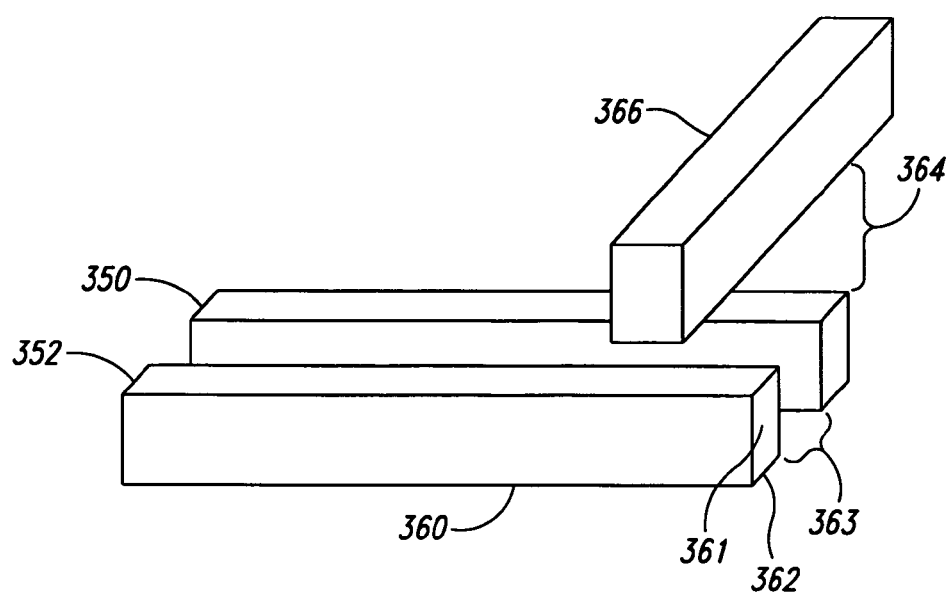
FIG. 3B is an illustration of an exemplary set of channels in a block used as an ultrasonic inspection reference standard according to one embodiment of the present invention.

FIG. 3B is an illustration of an exemplary set of channels in a block used as an ultrasonic inspection reference standard according to one embodiment of the present invention. FIG. 3B shows a set of channels 350, 352, and 366. Channel 352 can have a three-dimensional rectangular shape and includes a width 362, a height 361 and a length 360. In an embodiment of the present invention, all channels within block 300 can have the same width, height and length. In another embodiment of the present invention, the width, height and length of the channels within block 300 can vary. FIG. 3B also shows a distance 363 between channel 352 and an adjacent channel 350. In an embodiment of the present invention, the distance 363 between all channels of the same set within block 300 is equal. In another embodiment of the present invention, the distance 363 between each pair of channels of the same set within block 300 can vary.

FIG. 3B also shows a vertical distance 364 between channels 350, 352 and a channel 366, which is located in a separate plane from channels 350, 352 and belongs to a separate set of channels than the set of channels 350, 352. In an embodiment of the present invention, the vertical distance 364 between vertically adjacent sets of channels within block 300 is equal. In another embodiment of the present invention, the vertical distance 364 between vertically adjacent sets of channels within block 300 can vary.

In one embodiment of the present invention, the shape of channels 350, 352 and 366 includes at least one flat surface. Examples of such shapes include a triangle shape, a semicircular shape, a square shape, a rectangular shape and a pentagon shape. In this embodiment, the at least one flat surface of each channel of the same set (i.e., channels that are co-planar, such as channels 350 and 352) is co-planar. That is, each channel of the same set includes a flat surface that is co-planar.

Figure 3C:
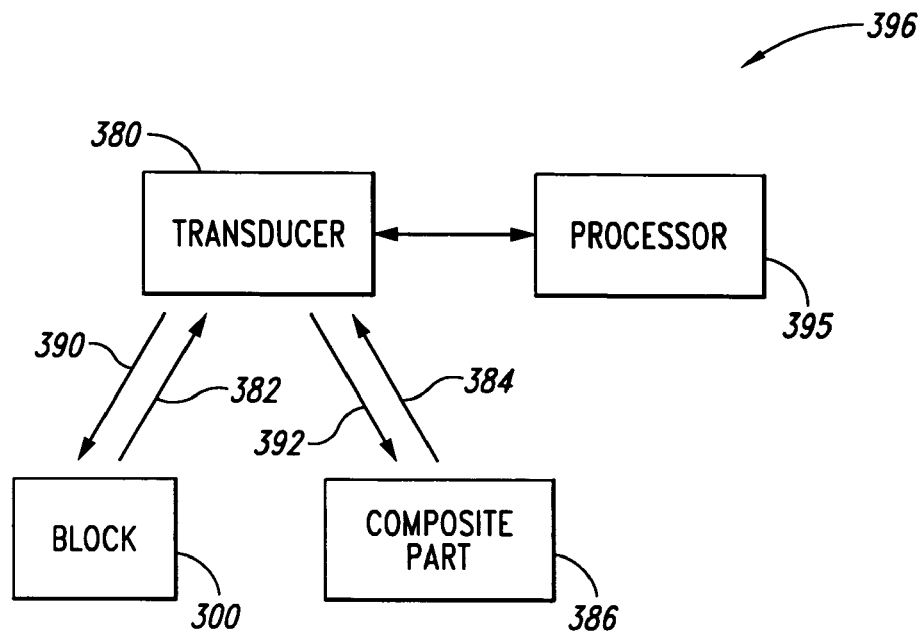
FIG. 3C is a block diagram of a system for inspecting composite materials, according to one embodiment of the present invention.

FIG. 3C is a block diagram of a system 396 for inspecting composite materials, according to one embodiment of the present invention. The system 396 includes a non-destructive ultrasonic apparatus 380, such as a transducer, a through transmission transducer, a pulse echo transducer or an eddy current transducer. The apparatus 380 can be used to produce ultrasonic emanations or waves 390 that are directed upon an ultrasonic reference standard, such as block 300. The ultrasonic emanations 390 are reflected by the block 300 and return to the apparatus 380 in the form of an attenuation reading 382. Next, the apparatus 380 can be used to produce ultrasonic emanations or waves 392 that are directed upon a composite part 386. The ultrasonic emanations 392 are reflected by the composite part 386 and return to the apparatus 380 in the form of an attenuation reading 384. Finally, the reading 382 and the reading 384 are compared by a processor 395.

Figure 4:
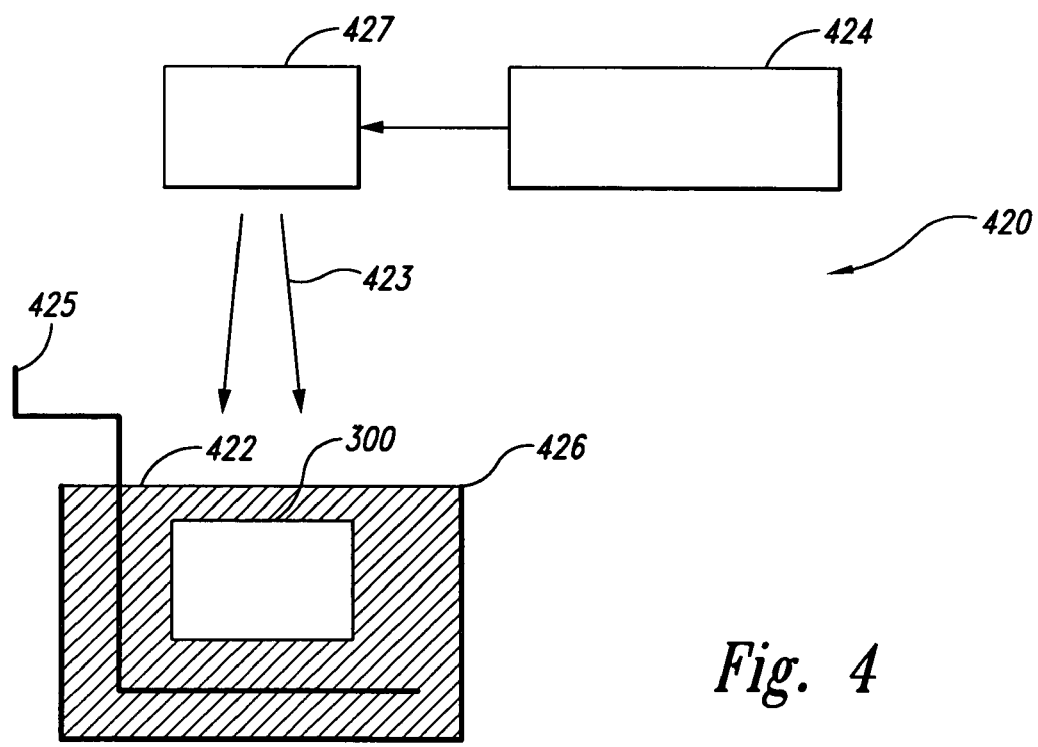
FIG. 4 is a block diagram illustrating a stereo lithography process for manufacturing composite materials according to another embodiment of the present invention.

The ultrasonic inspection reference standard represented by block 300 may be manufactured using a stereo lithography process as shown in FIG. 4. FIG. 4 is a block diagram illustrating a stereo lithography process for manufacturing composite materials according to another embodiment of the present invention. The stereo lithography process 420, as illustrated in FIG. 4, may produce an ultrasonic inspection reference standard, such as block 300, directly from a 3D CAD (computer-aided design) model.

The surface of a liquid photopolymer 422 is solidified layer-by-layer using a laser beam 423 emitted by a laser 424. When the laser beam 423 hits the liquid photopolymer 422, it solidifies the resin. When a layer is fully traced, a movable table 425 is than lowered in the vat 426. A scanner system 427 directs the laser beam 423 according to a loaded CAD model. The self-adhesive property of the material causes the layers to stick with each other and in this way a three-dimensional part, such as block 300, is formed in multi-layers.

The stereo lithography process 420 can be very accurate and suitable for smooth surface finished parts. Parts manufactured using the stereo lithography process 420 may be used, for example, for conceptual designs, product verification, pattern making. The stereo lithography process 420 may be used, for example, for rapid prototyping. If the reference standard 300 were manufactured using the stereo lithography process 420 as shown in FIG. 4, the reference standard 300 would be manufactured from a photo-polymer resin. Using the stereo lithography process 420 may further enable the manufacture of ultrasonic inspection reference standards, such as the reference standard 300, with a varying thickness and with geometries that resemble the fiber-reinforced part to be inspected. It may further be possible to use a resin that can be cast to manufacture the reference standard 300. Such resin may be preferably the same resin as used in the fiber-reinforced composite part to be tested. Casting a resin may include the steps of building a mold, pouring a cast resin into the mold, and baking the resin at cure temperature. Both methods to manufacture the ultrasonic inspection reference standard 300 from a fiber-free or fiber-inclusive polymer resin may not require any tooling. Manufacturing the ultrasonic inspection reference standard 300 may not be limited to the above-described methods.

Figure 5:
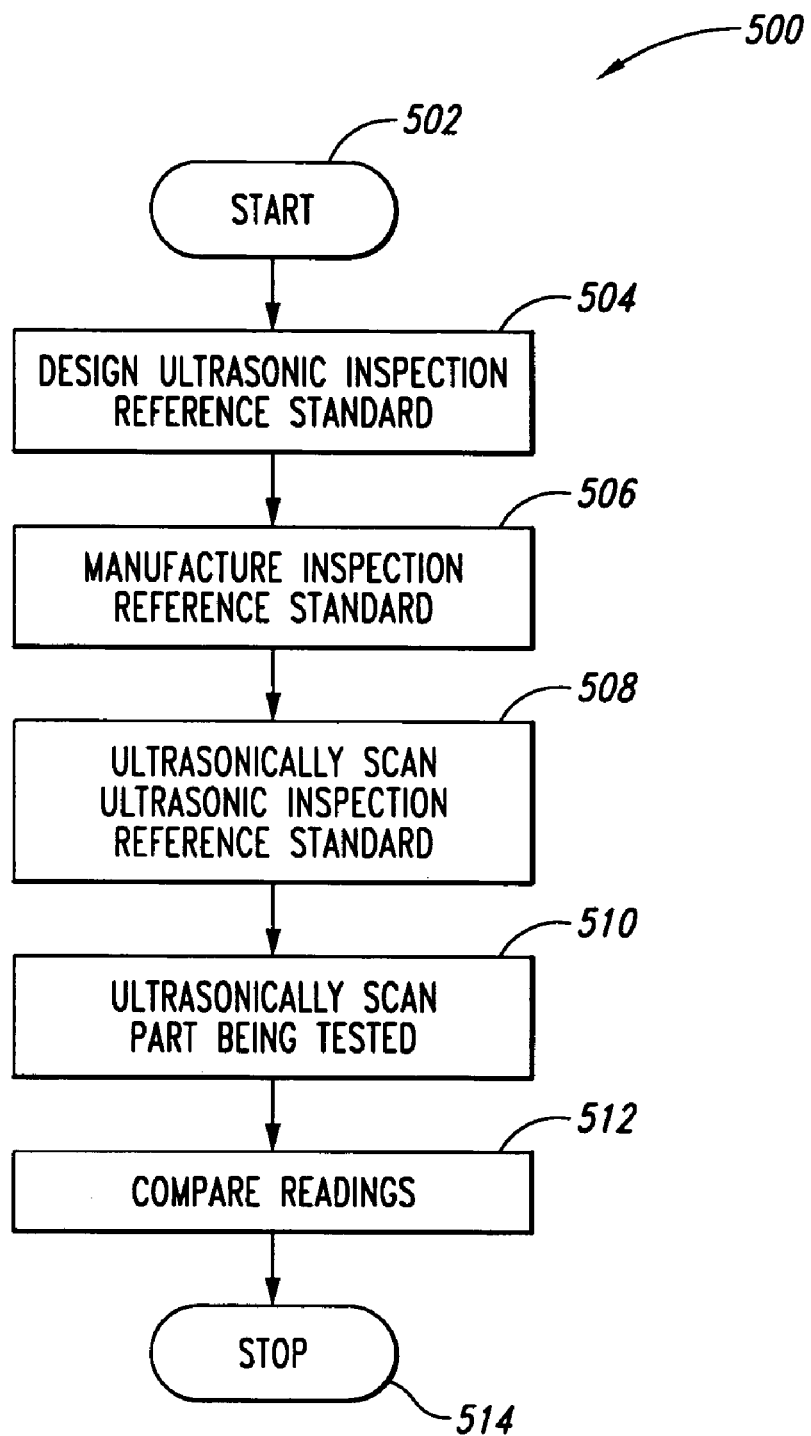
FIG. 5 is a flow chart of an ultrasonic inspection process for composite materials according to another embodiment of the present invention.

FIG. 5 is a flow chart 500 of an ultrasonic inspection process for composite materials according to another embodiment of the present invention. Flow chart 500 beings with step 502 and proceeds immediately to step 504. In step 504, an ultrasonic inspection reference standard, such as block 300, is designed. Step 504 can include designing the ultrasonic inspection reference standard by creating a 3D CAD model. The general process of designing an engineering element by creating a CAD model is known to one of ordinary skill in the art.

In step 506, the ultrasonic inspection reference standard can be manufactured, for example, as described by the process of FIG. 4. Thus, the ultrasonic inspection reference standard may be manufactured by using the stereo lithography process 420 as described in FIG. 4. Alternatively, a cast ultrasonic inspection reference standard may also be manufactured by using a casting method. The process of casting a material is well known to one of ordinary skill in the art. In another embodiment of the present invention, the ultrasonic inspection reference standard can be manufactured using an alternative approach.

Next, in step 508, the ultrasonic inspection reference standard can be ultrasonically scanned using an ultrasonic inspection technique, such as pulse-echo and through-transmission technique. The scanning step 508 produces a reading, such as reading 382 of FIG. 3C. In step 510, a composite part can be ultrasonically scanned thereby producing another reading, such as reading 384.

In step 512, the reading 384 from scanning the composite part in step 510 can be compared with the reading 382 obtained from scanning the ultrasonic inspection reference standard in step 508. In one example, if the reading 384 of the composite part is identical or similar (i.e., within a predefined range, such as within 0.1%) to the reading 382 of the inspection reference standard, the porosity level of the composite part is deemed to be the same as the porosity percentage associated with the inspection reference standard, e.g., the porosity percentage associated with the block 300. Likewise, if the reading 384 of the composite part is greater than the reading 382 of the inspection reference standard, the porosity level of the composite part is deemed to be greater than the porosity percentage associated with the inspection reference standard. In another example, if the reading 384 of the composite part is different than the reading 382 of the inspection reference standard, then another inspection cycle is initiated with a separate inspection reference standard or block until the reading 382 of the inspection reference standard and the reading 384 of the composite part are similar or identical.

In step 514, the control flow of flowchart 500 stops.

It should be understood, of course, that the foregoing relates to exemplary embodiments of the invention and that modifications may be made without departing from the spirit and scope of the invention as set forth in the following claims.

We claim:

1. A system for inspecting composite materials, comprising:
    an ultrasonic inspection apparatus for ultrasonically scanning a material comprising a composite material to be inspected; and
    a block comprising a reference composite material corresponding to the composite material to be tested, the block including:
        a first plurality of rectangular parallel channels within the block, wherein each channel includes a flat surface and each flat surface is co-planar; and
        a second plurality of rectangular parallel channels within the block, perpendicular to the first plurality of channels, wherein each channel of the second plurality of channels includes a flat surface and each flat surface is co-planar and wherein the second plurality of channels is located on a separate plane as the first plurality of channels.

2. The system of claim 1, wherein a porosity of the reference composite material ranges from about zero to about eight percent.

3. The system of claim 2, further comprising a plurality of blocks, each block of the plurality having a porosity different from other blocks of the plurality, the porosity of each block ranging from about zero to about eight percent.

4. The system of claim 3, wherein the plurality of blocks comprises from about five to about eight blocks.

5. The system of claim 1, wherein the acoustic properties of the composite material are similar to the acoustic properties of the block.

6. The system of claim 1, wherein the ultrasonic inspection apparatus comprises any one of a through transmission transducer, a pulse echo transducer and an eddy current transducer.

7. An ultrasonic inspection process for composite materials, comprising the steps of:
    inspecting an ultrasonic inspection reference standard with an ultrasonic technique, the ultrasonic inspection reference standard comprising a block comprising a composite material, wherein the block includes a first plurality of parallel rectangular-shaped channels within the block and a second plurality of parallel rectangular-shaped channels within the block, wherein the second plurality of channels extend at about a ninety degree angle to the first plurality of channels and wherein the second plurality of channels is located on a separate plane as the first plurality of channels;
    inspecting a composite part with the ultrasonic technique; and
    comparing results of the inspecting of the ultrasonic inspection reference standard with results of the inspecting of the composite part.

8. The ultrasonic inspection process of claim 7, further comprising the step of:
    determining whether the composite part is utilizable based on the comparing step.

9. The ultrasonic inspection process of claim 7, further comprising:
    associating a porosity percentage with the ultrasonic inspection reference standard.

10. The ultrasonic inspection process of claim 7, wherein the ultrasonic inspection reference standard comprises a fiber and a resin.

11. The ultrasonic inspection process of claim 10, wherein the ultrasonic inspection reference standard comprises graphite.

12. The ultrasonic inspection process of claim 10, wherein the ultrasonic inspection reference standard is manufactured using a stereo lithography process.

* * * * *